US010905392B2

(12) United States Patent
Sklair-Levy et al.

(10) Patent No.: US 10,905,392 B2
(45) Date of Patent: *Feb. 2, 2021

(54) MAMMOGRAPHY APPARATUS

(71) Applicant: Tel HaShomer Medical Research, Infrastructure and Services Ltd., Ramat Gan (IL)

(72) Inventors: Miriam Sklair-Levy, Mevasseret Zion (IL); Arnaldo Mayer, Ramat Hasharon (IL); Shmuel Yitzhak Pfeffer, Lod (IL)

(73) Assignee: Tel HaShomer Medical Research, Infrastructure and Services Ltd., Ramat Gan. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/699,660

(22) Filed: Dec. 1, 2019

(65) Prior Publication Data
US 2020/0138392 A1 May 7, 2020

Related U.S. Application Data

(63) Continuation of application No. 15/750,514, filed as application No. PCT/IB2016/054707 on Aug. 4, 2016, now Pat. No. 10,499,866.
(Continued)

(51) Int. Cl.
*A61B 6/00* (2006.01)
*G06T 7/00* (2017.01)
(Continued)

(52) U.S. Cl.
CPC ............ *A61B 6/502* (2013.01); *A61B 6/0414* (2013.01); *A61B 6/0435* (2013.01); *A61B 6/481* (2013.01);
(Continued)

(58) Field of Classification Search
CPC ....... A61B 6/0414; A61B 6/0435; A61B 6/12; A61B 6/481; A61B 6/502; A61B 6/5205;
(Continued)

(56) References Cited

U.S. PATENT DOCUMENTS

| 10,499,866 | B2* | 12/2019 | Sklair-Levy | G06T 7/44 |
| 2010/0111392 | A1* | 5/2010 | Valadez | G06K 9/3233 |
| | | | | 382/131 |
| 2012/0257808 | A1* | 10/2012 | Spitzer | G06T 5/008 |
| | | | | 382/131 |

* cited by examiner

*Primary Examiner* — Mark R Gaworecki
(74) *Attorney, Agent, or Firm* — A.C. Entis-IP Ltd.; Allan C. Entis

(57) ABSTRACT

Apparatus for diagnosing breast cancer, the apparatus comprising a controller having a set of instructions executable to: acquire a contrast enhanced region of interest (CE-ROI) in an X-ray image of a patient's breast, the X-ray image comprising X-ray pixels that indicate intensity of X-rays that passed through the breast to generate the image; determine a texture neighborhood for each of a plurality of X-ray pixels in the CE-ROI, the texture neighborhood for a given X-ray pixel of the plurality of X-ray pixels extending to a bounding pixel radius of BPR pixels from the given pixel; generate a texture feature vector (TF) having components based on the indications of intensity provided by a plurality of X-ray pixels in the CE-ROI that are located within the texture neighborhood; and use a classifier to classify the texture feature vector TF to determine whether the CE-ROI is malignant.

13 Claims, 8 Drawing Sheets

Related U.S. Application Data

(60) Provisional application No. 62/201,774, filed on Aug. 6, 2015, provisional application No. 62/260,549, filed on Nov. 29, 2015.

(51) Int. Cl.

| | |
|---|---|
| *G06T 7/40* | (2017.01) |
| *G06K 9/50* | (2006.01) |
| *G06K 9/48* | (2006.01) |
| *G06K 9/46* | (2006.01) |
| *G06T 7/11* | (2017.01) |
| *G06T 7/13* | (2017.01) |
| *A61B 6/04* | (2006.01) |
| *G06T 7/44* | (2017.01) |
| *A61B 6/12* | (2006.01) |

(52) U.S. Cl.
CPC .......... *A61B 6/5205* (2013.01); *G06K 9/4642* (2013.01); *G06K 9/48* (2013.01); *G06K 9/50* (2013.01); *G06T 7/0012* (2013.01); *G06T 7/11* (2017.01); *G06T 7/13* (2017.01); *G06T 7/44* (2017.01); *A61B 6/12* (2013.01); *G06K 2209/05* (2013.01); *G06T 2207/10116* (2013.01); *G06T 2207/20081* (2013.01); *G06T 2207/30068* (2013.01)

(58) Field of Classification Search
CPC .......... G06K 9/4642; G06K 9/48; G06K 9/50; G06T 2207/10116; G06T 2207/20081; G06T 2207/30068; G06T 7/0012; G06T 7/11; G06T 7/13; G06T 7/44
See application file for complete search history.

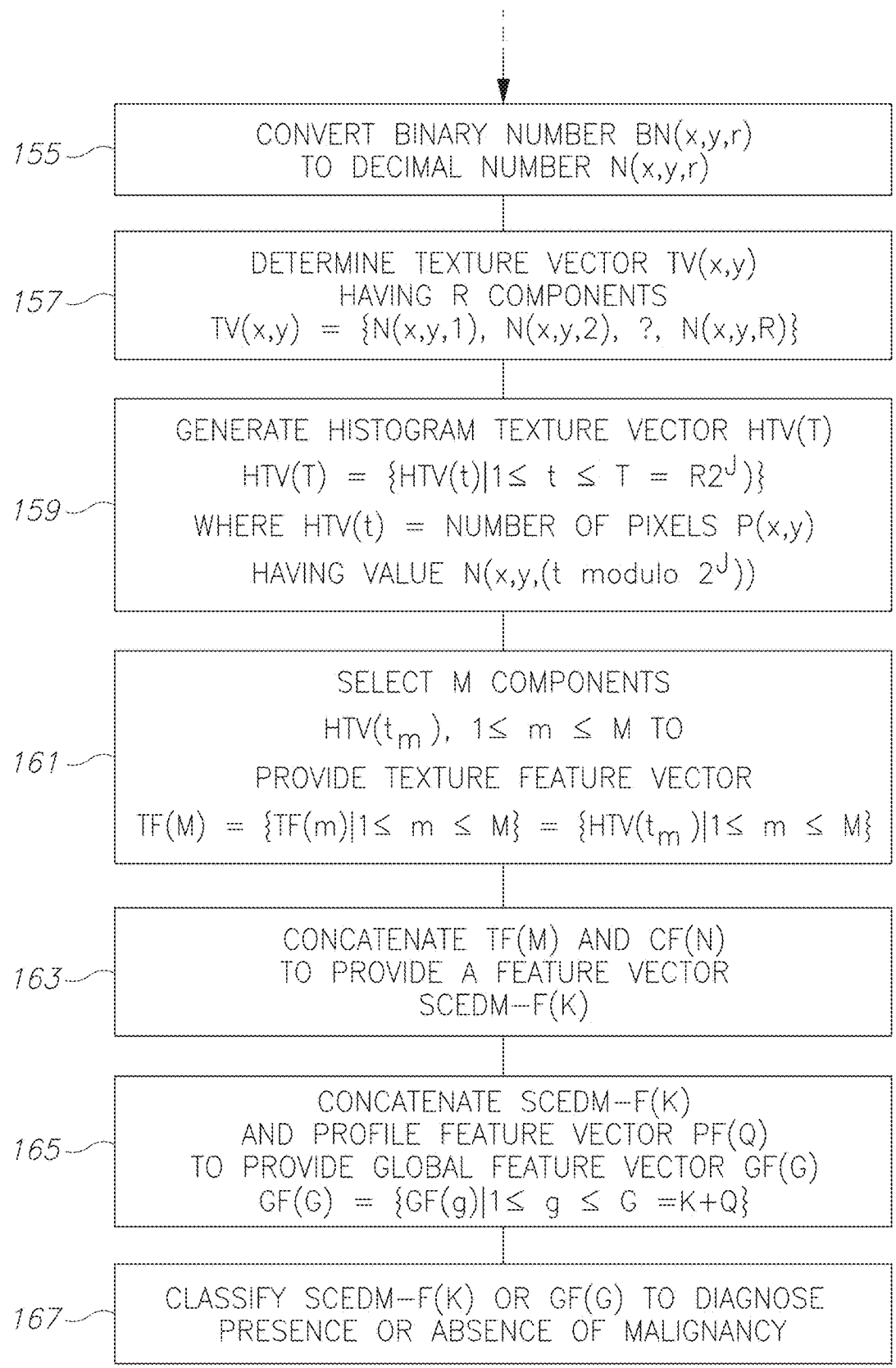
FIG.2A (cont. 1)

MAMMOGRAPHY APPARATUS

RELATED APPLICATIONS

The present application is a continuation of U.S. application Ser. No. 15/750,514 filed on Feb. 6, 2018 as a National Phase of PCT Application No. PCT/IB2016/054707 filed on Aug. 4, 2016, which claims the benefit under 35 U.S.C. 119(e) of U.S. Provisional Application 62/201,774 filed on Aug. 6, 2015 and U.S. Provisional Application 62/260,549 filed on Nov. 29, 2015 the disclosures of which are incorporated herein by reference.

TECHNICAL FIELD

Embodiments of the disclosure relate to apparatus and methods for diagnosing breast cancer.

BACKGROUND

X-ray imaging of the human breast to detect malignancies has been clinically available since about 1970. As might very well be expected, since then, over the period of almost half a century the technology has undergone a number of changes and refinements. Initially, X-ray images were captured on film. Today X-ray breast images are directly captured by arrays of small X-ray detectors which convert intensity of X-rays incident on the detectors to electrical signals. The electrical signals are digitized to provide digital representations of the images that are stored in computers for later diagnoses.

A relatively recent change in X-ray breast imaging technology that was made practical by digital X-ray imaging is referred to as spectral contrast enhanced digital mammography (SCEDM). In SCEDM a patient is injected with a contrast agent that is preferably taken up by cancerous lesions in the patient's breast. The breast is exposed to X-rays at two different energies, typically a relatively low X-ray energy at which the contrast agent is a relatively poor absorber of X-rays and a relatively high X-ray energy at which the contrast agent is a relatively good absorber of X-rays. The exposures to the high and low energy X-rays provide high and low energy X-ray digital images respectively of the breast. The images are digitally subtracted to provide a "subtracted image" in which concentrations of the contrast agent in the breast, and thereby malignant lesions in the breast, generally have enhanced contrast and visibility. In particular, for dense breast tissues, known to be relatively opaque in classical mammography, normal breast tissue becomes substantially transparent in the subtracted image, enhancing contrast of lesions that in conventional non-subtracted X-ray images may be difficult to discern. Typically, the contrast agent used to acquire the high and low X-ray images is an iodine based contrast agent, and the low energy X-rays have an energy below the k-edge of iodine and the high energy X-rays have an energy above the k-edge of iodine.

Although SCEDM has the potential to improve sensitivity of mammography, in practice, a relatively large number of biopsies is performed on lesions detected in SCEDM images that turn out to be benign. More than 60% of the biopsies triggered by a lesion detected in SCEDM are actually performed on benign lesions. The relatively large number of biopsies that turn out to be unnecessary imposes a relatively high financial cost and psychological burden on patients and society.

SUMMARY

An aspect of an embodiment of the disclosure relates to providing apparatus for diagnosing presence of breast malignancies in a patient's breast, the apparatus comprising an X-ray imager configured to acquire an SCEDM image of the breast and a processor configured to process the image to provide a determination of the presence of malignancies. In an embodiment, the processor processes the SCEDM image to generate an image feature vector for a contrast enhanced region of interest (CE-ROI) in the SCEDM that is a function of morphology and/or texture of the CE-ROI. The processor uses the CE-ROI feature vector, to provide a determination as to whether or not the CE-ROI comprises a malignancy. A determination may comprise an estimate of a probability that a CE-ROI comprises a malignancy. The processor may also use a context feature vector, hereinafter also referred to as a "profile feature vector", based on a personal profile of the patient, to provide the determination as to whether or not the CE-ROI comprises a malignancy. In an embodiment, the processor operates on the CE-ROI feature vector and/or the profile feature vector in accordance with a classifier to determine whether or not the CE-ROI comprises a malignancy. Optionally, the classifier comprises a support vector machine (SVM) or a neural network.

Experiments carried out on SCEDM images acquired from actual patients and for which biopsies were performed indicate that apparatus, in accordance with an embodiment of the disclosure, hereinafter also referred to as an X-ray Breast Imager (XBI) may provide sensitivity to detecting breast malignancies that ranges from about 90% to 100% with associated specificities that range respectively from about 70% to about 37%. For an embodiment for which sensitivity is equal to about 98.1% associated specificity was equal to about 53.7%. It is noted that human inspection of SCEDM images to detect breast malignancies typically provide sensitivity of about 90%-95% and associated specificity of about 55%-65%.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

DETAILED DESCRIPTION

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which the embodiment is intended. Wherever a general term in the disclosure is illustrated by reference to an example instance or a list of example instances, the instance or instances referred to, are by way of non-limiting example instances of the general term, and the general term is not intended to be limited to the specific example instance or instances referred to. Unless otherwise indicated, the word "or" in the description and claims is considered to be the inclusive "or" rather than the exclusive or, and indicates at least one of, or any combination of more than one of items it conjoins.

Figure 1A:
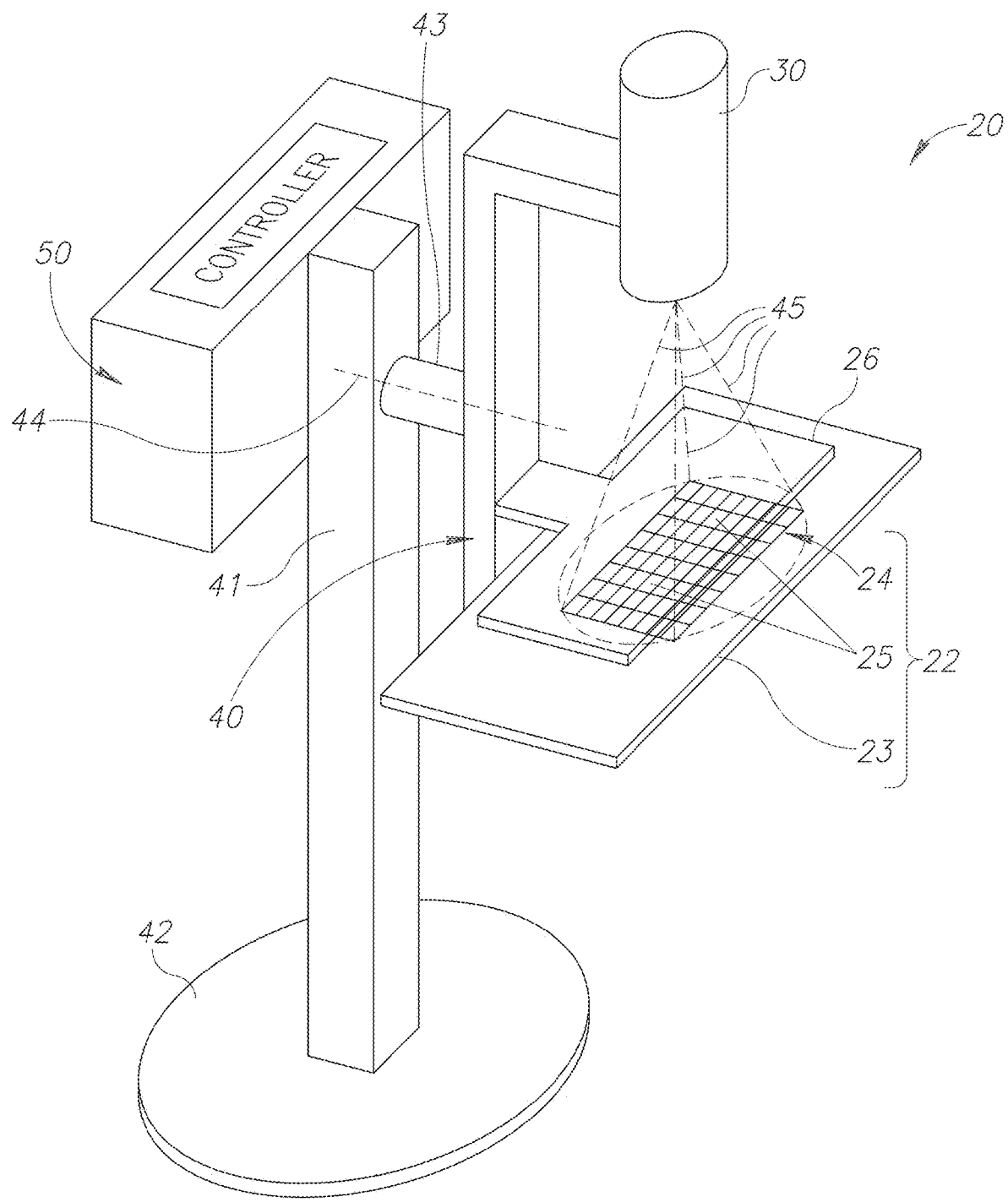
FIG. 1A schematically shows an X-Ray breast imager (XBI) for acquiring SCEDM images of a breast, in accordance with an embodiment of the disclosure.

FIG. 1A schematically shows an X-Ray breast imager (XBI) 20 for acquiring SCEDM images of a breast, in accordance with an embodiment of the disclosure. XBI 20 optionally comprises a controller 50, an X-ray source 30 configured to generate a beam of X-rays for acquiring SCEDM images of a breast, and a breast holder 22 for holding and positioning a breast in the X-ray beam provided by the X-ray source. X-rays generated by X-ray source 30 are schematically indicated by dashed lines 45. Embodiments of controller 50 may comprise any electronic and/or optical, memory, processing, and/or control circuitry advantageous for providing controller functionalities. By way of example, controller 50 may, comprise any one or any combination of more than one of, a microprocessor, an application specific circuit (ASIC), field programmable array (FPGA) and/or system on a chip (SOC). The controller may comprise any one or any combination of more than one of a flash memory, random access memory (RAM), read only memory (ROM), and/or erasable programmable read-only memory (EPROM). And whereas controller 50 is shown in FIG. 1A as a single localized entity, the controller may be configured as a distributed entity or at least in part a cloud based entity.

Breast holder 22 comprises a breast support plate 23 and a breast compressor plate 26 for compressing a breast positioned on support plate 23 in preparation for exposure to X-rays 45 to acquire an X-ray image of the breast. Breast support plate 23, comprises a digital X-ray camera 24 having an array of X-ray sensors 25, each sensor 25 operable to generate electronic signals responsive to intensity of X-rays 45 that pass through the breast held in breast holder 22. Compressor plate 26 is made from a material such as a suitable plastic that is substantially transparent to X-rays 45. X-ray source 30 and breast holder 22 are optionally mounted to a support beam 40 attached to a column support 41 by a shaft 43. Column support 41 is attached to a base 42 for floor mounting XBI 20.

Support beam 40 and shaft 43 may be configured to slide up and down along column support 41 to adjust height of breast holder 22 to a patient's height, and to enable the support beam to rotate about an axis of rotation, indicated by a dashed line 44, of shaft 43 so that X-Ray images of the breast, may be acquired from various angles. By way of example, support beam 40 is schematically shown in FIG. 1A oriented vertically parallel to column support 41 so that XBI 20 may acquire a Cranial-Caudal (CC) X-ray image of a breast. Rotation of support beam 40 away from the vertical enables XBI 20 to acquire a mediolateral-oblique (MLO) image views of the breast.

Figure 1B:
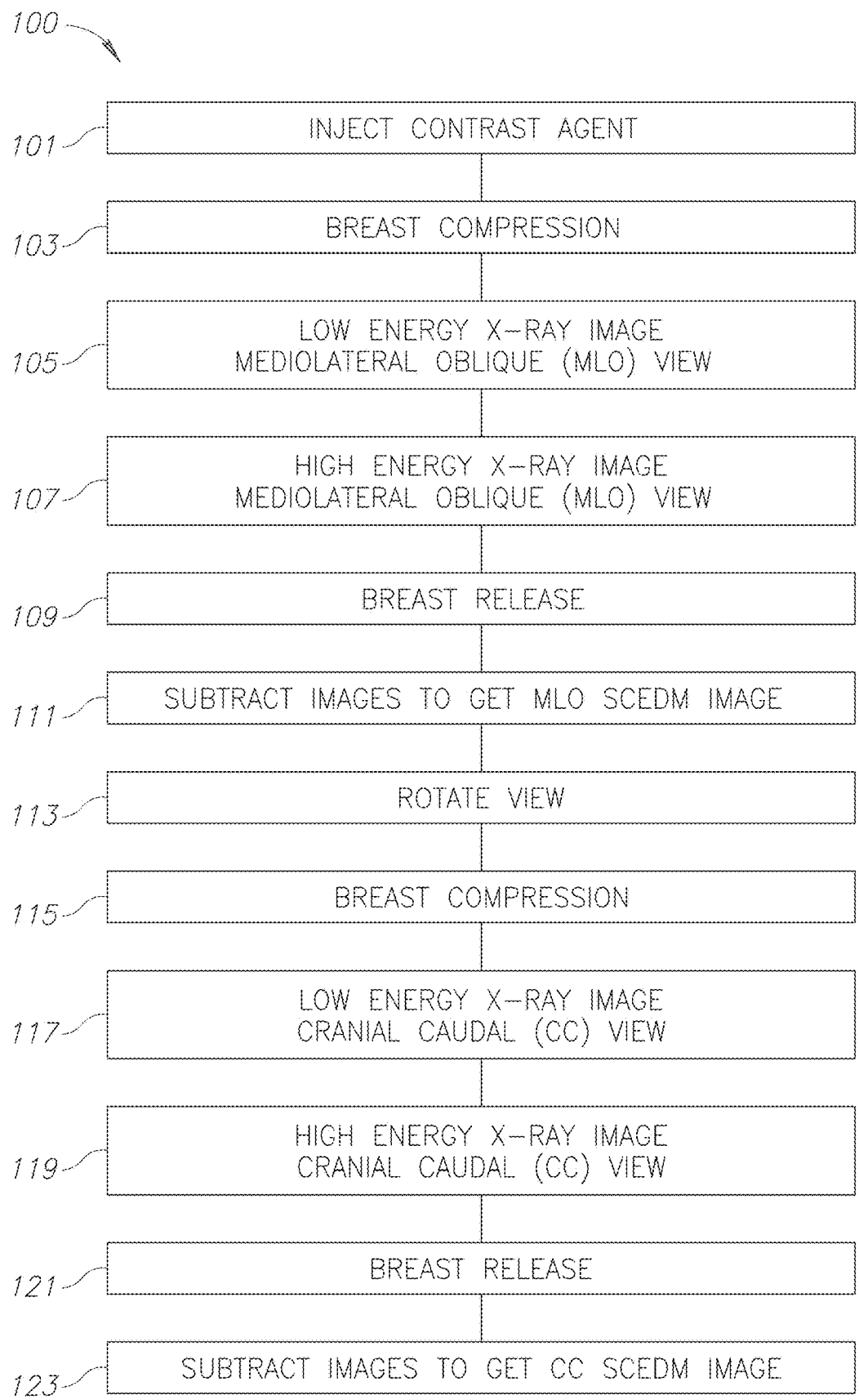
FIG. 1B shows a flow diagram in accordance with which the XBI schematically shown in FIG. 1A acquires SCEDM images, in accordance with an embodiment of the disclosure.

FIG. 1B shows a flow diagram 100 illustrating a procedure by which XBI 20 may operate to acquire SCEDM images of a breast (not shown). Initially, in block 101, a contrast agent, which is preferentially taken up in regions of increased vascularity, such as in growing tumors, is injected into a patient (not shown) in preparation for imaging a breast (not shown) of the patient. Optionally, in a block 103 the patient's breast is positioned between breast support plate 23 and breast compressor plate 26 and compressed, to even out the thickness of the breast tissue and avoid folding of the breast tissue which can obscure internal features of the breast, in preparation for acquiring, optionally, MLO X-ray images of the breast. For acquiring the MLO X-ray image support beam 40 shown in FIG. 1A is substantially perpendicular to column support 41 and parallel to the floor. In a block 105 controller 50 controls X-ray source 30 and digital X-ray camera 24 to expose the breast to low energy X-rays and acquire a low energy MLO X-ray image of the breast. In a block 107 the controller controls X-ray source 30 and X-ray camera 24 to expose the breast to high energy X-rays and acquire a high energy MLO X-ray image of the breast. The breast may then be released in a block 109 and controller 50 (FIG. 1A) may in a block 111 process the high and low energy X-ray images to provide a MLO SCEDM image by subtracting the low energy X-ray image from the high energy X-ray image. In a block 113 controller 50 may rotate support beam 40 of XBI 20 (FIG. 1A) so that it is parallel to support beam 41, as shown in FIG. 1A, to orient X-ray source 30 and breast holder 22 for X-ray imaging of the breast at a CC view. In a block 115 the breast is optionally again positioned between the breast support plate 23 and breast compressor plate 26, and the latter is moved towards breast support plate 23 to compress the breast and even out breast tissue. A series of two X-ray exposures are made of the breast to acquire a "low energy CC X-ray image", optionally in a block 117 and a "high energy CC X-ray image" optionally in a block 119. The breast may then be released in a block 121 and in a block 123 controller 50 processes the low and high CC X-ray images to generate a CC SCEDM image.

It is noted that contrast agents that preferentially accumulate in malignant lesions and are used in SCEDM breast imaging are generally iodinated agents. Therefore to acquire low energy images in SCEDM imaging of breast tissue the energy of the X-rays provided by X-ray source 30 in XBI 20 is below the k-edge of iodine. To acquire the high energy images the energy of X-rays provided by X-ray source 30 is above the k-edge of the iodine in the contrast agent.

Figure 3:
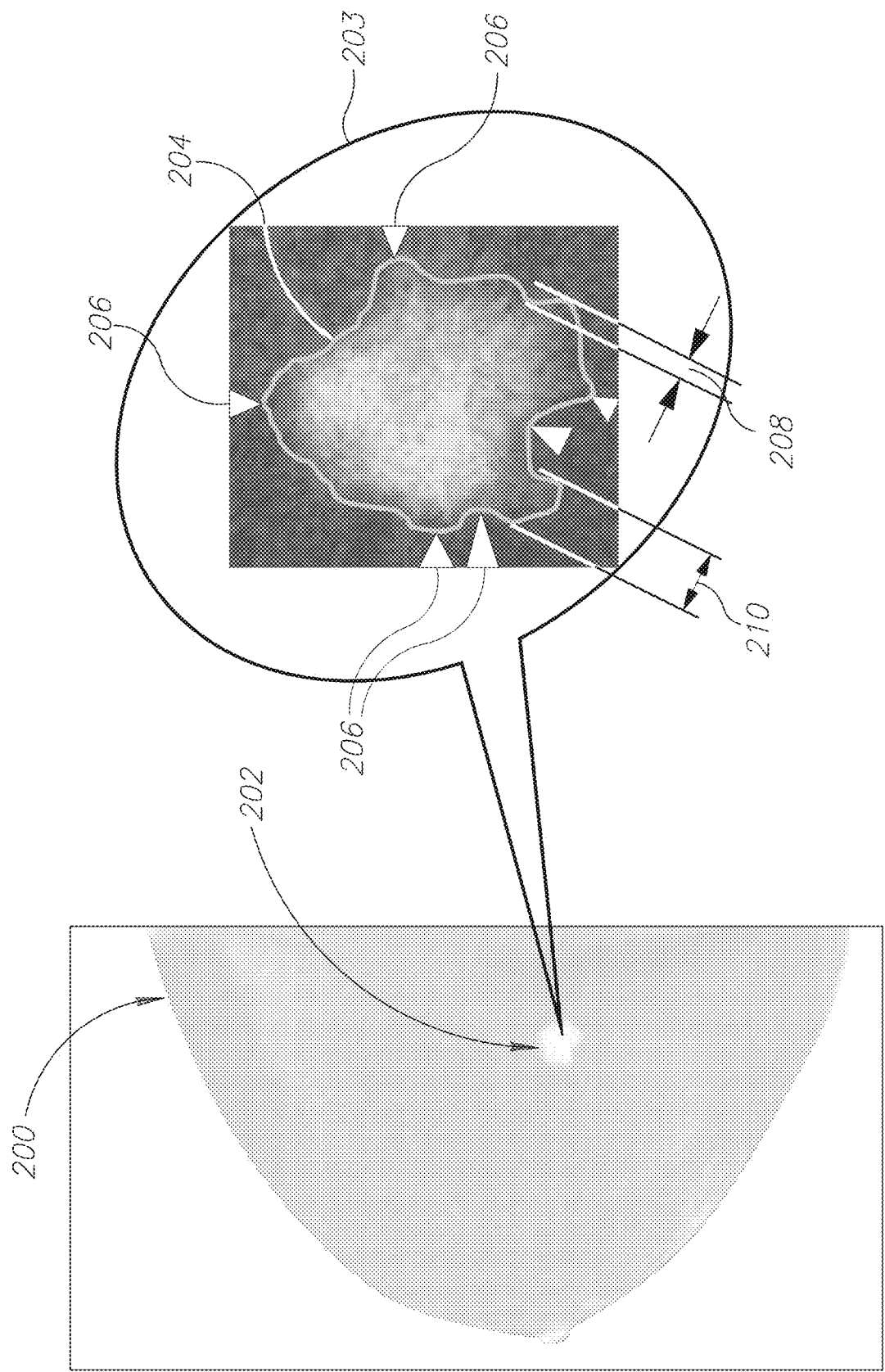
FIG. 3 schematically shows an SCEDM image of a breast comprising a contrast enhanced region of interest (CE-ROI) having a contour processed in accordance with the procedure flow diagram show in in FIG. 2 to provide a contour feature vector "CF" for diagnosing malignancy, in accordance with an embodiment of the disclosure.
Figure 4:
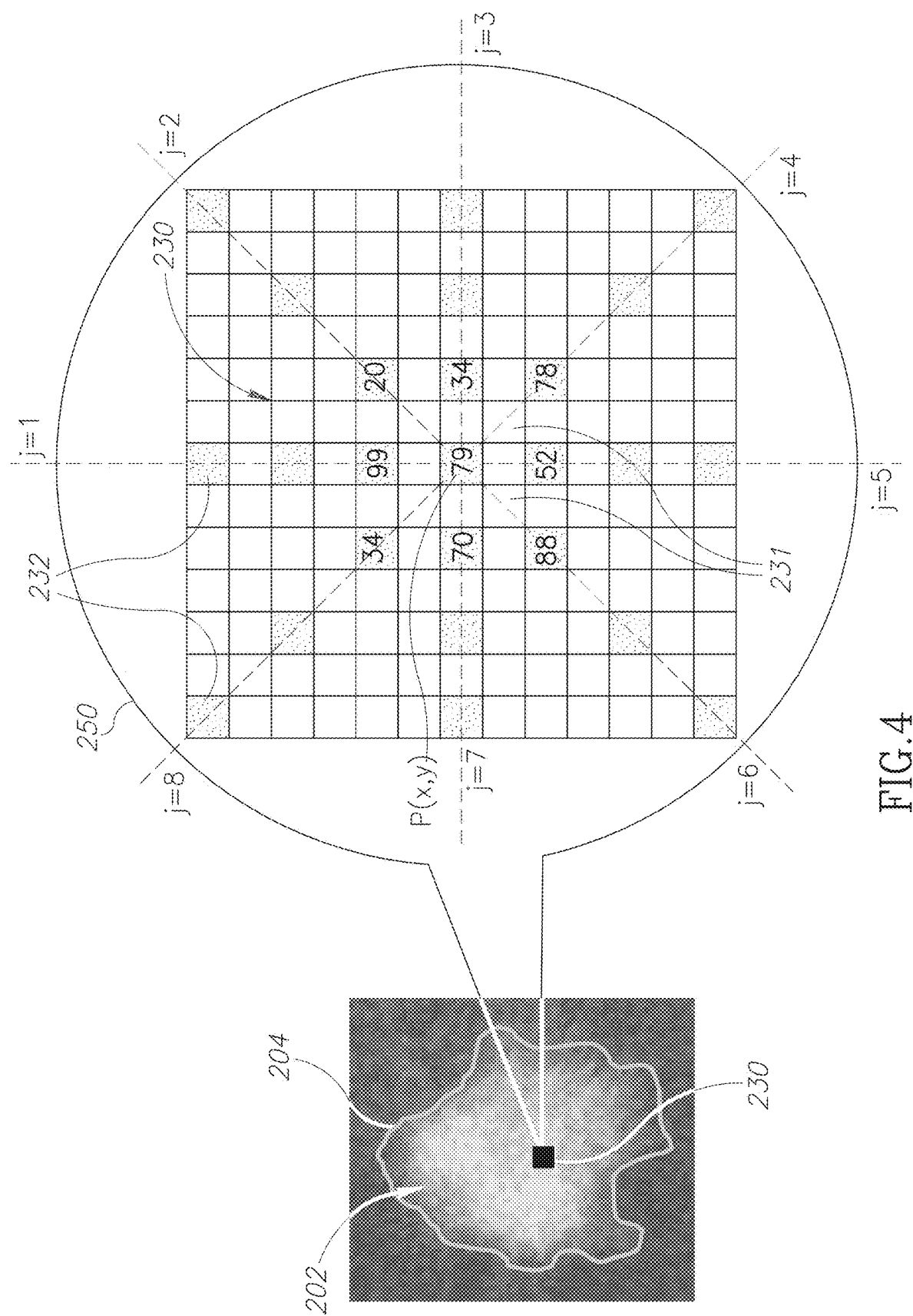
FIG. 4 schematically shows pixels that image the CE-ROI in the X-ray breast image shown in FIG. 3 and are processed in accordance with the procedure flow diagram show in in FIG. 2 to provide a texture feature vector "TF" for diagnosing malignancy, in accordance with an embodiment of the disclosure.

In an embodiment of the disclosure, controller 50 (FIG. 1A) may process an SCEDM X-ray image of a patient's breast acquired by XBI 20 to determine presence of a malignancy in accordance with a procedure illustrated by a flow diagram 140 shown in FIG. 2. The numerical label 140 may be used to refer to the procedure illustrated by flow diagram 140 as well as to the flow diagram. FIG. 3 shows an example SCEDM X-ray image 200 acquired for a breast of a patient. SCEDM X-ray image 200 exhibits a CE-ROI 202, shown greatly enlarged in FIG. 3 in an inset 203, that may comprise a malignancy and may be processed by controller 50 in accordance with procedure 140. FIG. 4 schematically shows pixels in a region of CE-ROI 202 greatly enlarged in an inset 250 to illustrate how they may be processed to provide a texture feature vector TF for use in diagnosing breast malignancy, in accordance with procedure 140. Features shown in FIGS. 3 and 4 may be referred to where relevant in the flow diagram of FIG. 2 by their labels in FIGS. 3 and 4.

In a block 141 of procedure 140 controller 50 may receive via a suitable user interface (not shown) to the controller, a segmentation of X-ray image 200 shown in FIG. 3 made by a medical practitioner that locates CE-ROIs, of which CE-ROI 202 is an example, in the image. Alternatively or additionally controller 50 may process the X-ray image using a suitable segmentation algorithm to locate CE-ROIs. In a block 143 a contour 204 of CE-ROI 202 may be determined. The contour may be determined automatically by controller 50 or may be manually determined and input to controller 50 by a user operating the interface to the controller.

Optionally, in a block 145, controller 50 processes contour 204 to provide components of a contour feature vector CF(N) characterizing the contour and having components CF(n), $1 \leq n \leq N$. Components CF(n) may comprise, by way of example, a length of contour 204, a number of turning points in the contour, entries in a histogram of heights of positive turning points, and entries in a histogram of widths of peaks in the contour.

Turning points in contour 204 are points along the contour at which a derivative as a function of a parameter measuring displacement along the contour is zero. A positive turning point is a point at which contour 204 is concave facing inwards to the area of CE-ROI 202 surrounded by the contour. A negative turning point is a point at which contour 204 is convex facing inwards to the area of CE-ROI 202. Example turning points in contour 204 are indicated by a triangle pointer 206 and may be referred to by the numeral 206. A height of a positive turning point 206 may be a distance between the positive turning point and an adjacent negative turning point along contour 204. An example height of a positive turning point is indicated in FIG. 3 by a distance 208. In accordance with an embodiment, entries in a histogram of heights of positive turning points 206 in contour 204 may be features of feature vector CF(N). A peak of contour 204 may be a segment of contour 204 between two negative turning points adjacent to and located on opposite sides of a positive turning point in the contour. Width of the may be a distance between points on the contour on opposite sides of the peak's positive turning point located at respective half heights to the peak's negative turning points. A peak width of contour 204 is indicated by a numeral 210. Entries in a histogram of peak widths in contour 204 may be features of feature vector CF(N) in accordance with an embodiment of the disclosure.

Optionally, in a block 147, for each X-ray pixel "P(x,y)" of X-ray image 200 located in CE-ROI 202 at row and column image coordinates (x,y) of the X-ray image, controller 50 determines a neighborhood, optionally referred to as a "texture neighborhood", of X-ray pixels in CE-ROI 202 for processing to determine a measure of texture of CE-ROI 202. The neighborhood, also referred to as a "texture neighborhood" extends "radially" a "radial pixel distance", also referred to as a "pixel radius" (PR), equal to a bounding pixel radius, "BPR", pixels in any direction from location (x,y) of X-ray pixel P(x,y).

FIG. 4 schematically shows a texture neighborhood 230 determined for an X-ray pixel P(x,y) in CE-ROI 202. Texture neighborhood 230 may extend to a radial pixel distance PR=BPR greater than or equal to about 25 pixels. Optionally, texture neighborhood 230 extends to a bounding pixel radius BPR of about 50 pixels or more. In an embodiment, texture neighborhood 230 extends to a bounding pixel radius BPR of at least about 75 pixels. A portion of texture neighborhood 230 that extends to a pixel radius PR of 7 pixels is schematically shown greatly enlarged in an inset 250 in the figure. X-ray pixels 231 are adjacent to pixel P(x,y) and are located at a pixel radius PR equal to 1 pixel from X-ray pixel P(x,y), while X-ray pixels 232 are located at a pixel radius PR=4 pixels from X-ray pixel P(x,y).

In a block 149, controller 50 selects X-ray pixels at R different pixel radii PR(r), $1 \leq r \leq R$, in texture neighborhood 230 for processing to determine a measure of texture for CE-ROI 202. Pixel radii PR(r) increase with increase in index r, and PR(R) is equal to the bounding pixel radius BPR of texture neighborhood 230. R may be equal to at least 2. Optionally, R is equal to or greater than about 10. Optionally R is greater than 20. By way of a numerical example, in the discussion that follows BPR for texture neighborhood 230 is assumed to be 64 pixels and R equal to 4. For convenience of presentation a pixel radius PR(r) may be referred to by its index as pixel radius r.

For each pixel radius r, $1 \leq r \leq R$, controller 50 selects, optionally a same number "J", of X-ray pixels S(x,y,r,j), $1 \leq j \leq J$ for processing. Optionally, J is equal to or greater than 4. In an embodiment J is equal to or greater than 8. By way of example, in FIG. 4, J=8, therefore eight X-ray pixels S(x,y,r,j) are selected from the X-ray pixels for each pixel radius, r=1, 2, 3, and 4. Selected pixels S(x,y,r,j) are indicated in FIG. 4 by shading and for convenience of presentation are shown for only pixel radii PR(1) and PR(2) as examples equal respectively to 2 pixels and 4 pixels. It is noted that practice of an embodiment of the disclosure is not limited to pixel radii PR(1)=2 and PR(2)=4. In an embodiment, by way of numerical example, for texture neighborhood 230 having BPR=64 and R=4 as noted above, pixel radii PR(1), PR(2), PR(3), and PR(4) in the texture neighborhood may be equal to 15, 30, 45 and 70 pixels respectively. Optionally, the selected pixels S(x,y,r,j) are symmetrically located around pixel P(x,y), along straight lines extending from pixel P(x,y). Optionally, selected pixels S(x,y,r,j) are located along lines extending from pixel P(x,y) every 45°, at angles (j−1)45° respectively. The lines are labeled with the value of the index j of the X-ray pixels S(x,y,r,j) associated with the lines. Selected X-ray pixels having index j=1, that is pixels S(x,y,r,1), lie along a 12 o'clock direction, and angles increase with increase in j in a clockwise direction.

In a block 151 controller 50 assigns a binary number 0 or 1, to each selected X-ray pixel S(x,y,r,j), depending on whether intensity of incident X-rays represented by a gray level of the selected X-ray pixel is respectively less than or greater than incident X-ray intensity represented by a gray level of pixel P(x,y). Let P(x,y) and S(x,y,r,j), in addition to identifying particular X-ray pixels in CE-ROI 202, represent intensity of X-rays that gray levels of the identified pixels respectively represent. Then the calculation performed in block 151 may be represented in symbols as: IF (S(x,y,r,j) <P(x,y), b(x,y,r,j)=0; otherwise, b(x,y,r,j)=1).

By way of example, arbitrary gray levels are shown in FIG. 4 for X-ray pixel P(x,y) and selected X-ray pixels S(x,y,1,j) that are located at pixel radius r=1 (that is PR(1)=2 pixels) from P(x,y). The arbitrary gray level for pixel P(x,y) is 79, and gray levels for selected X-ray pixels S(x,y,1,1)-S(x,y,1,8) are 99, 20, 34, 78, 52, 88, 70, 34 respectively. The selected X-ray pixels (S(x,y,1,j) are therefore assigned in block 151 corresponding binary numbers b(x,y,1,1), . . . , b(x,y,1,8) that are respectively equal to 1, 0, 0, 0, 0, 1, 0, 0.

Optionally, in a block 153 controller 50 assigns a binary number BN(x,y,r) comprising J bits for each pixel radius r in CE-ROI 202. A j-th bit of binary number BN(x,y,r) is equal to b(x,y,r,j) and a most significant bit in the binary number is optionally b(x,y,r,1). For example, for CE-ROI 202, BN(x,y,1) is determined from the binary numbers b(x,y,1,1)-b(x,y,1,8) discussed above, and is equal to 10000100. In a subsequent block 155, the controller may convert each binary number BN(x,y,r) to a decimal number N(x,y,r) that may assume any of $2^J$ values between 0 and ($2^J-1$). And in a block 157, the controller assigns an R dimensional texture vector TV(x,y) for X-ray pixel P(x,y) having R components: N(x,y,1), N(x,y,2), . . . , N(x,y,R). For CE-ROI 202 having R=4, and J=8 selected X-ray pixels S(x,y,r,j) for each pixel radius r, the decimal number N(x,y,r) may assume any of 256 values between and inclusive of 0 and 255, and TV(x,y) for X-ray pixel P(x,y) has 4 components.

In a block 159, controller 50 may generate a histogram HTV(T) of the texture vectors TV(x,y) determined for optionally all X-ray pixels P(x,y) having locations (x,y) in the area of CE-ROI 202. HTV(T) has T=$R2^J$ bins, and may be written as the set HTV(T)={HTV(t)|1≤t≤T=$R2^J$}, where HTV(t) is the value of a t-th bin of the histogram. A value HTV(t) is equal to a number of X-ray pixels P(x,y) in CE-ROI 202 having a decimal value N(x,y,(t modulo $2^J$). By way of example, for R=4 and J=8 the number of bins T is equal to 1024.

In an embodiment of the disclosure, optionally in a block 161, controller 50 selects "M" bins from the T bins of HTV(T) as components of a texture feature vector TF(M) for use in diagnosing malignancy in the breast imaged in X-ray image 200 (FIG. 3). In a block 163 the controller optionally generates an SCEDM feature vector, "SCEDM-F(•)" for CE-ROI 202 responsive to contour feature vector CF(N) and/or texture feature vector TF(M) to diagnose malignancy in the CE-ROI. Optionally, SCEDM-F(•) is a K dimensional feature vector SCEDM-F(K), which may be referred to as a feature vector CF-TF, having dimension K=(N+M) generated by concatenating CF(N) and texture feature vector TF(M).

In a block 165, controller 50 may concatenate SCEDM-F(K) with a Q dimensional profile feature vector PF(Q) of the patient for which X-ray image 200 was acquired to generate a G=(K+Q) dimensional global feature vector "GF(G)" for diagnosing malignancy in CE-ROI 202. Profile feature vector PF(Q) may comprise any one or any combination of more than one of personal data components, such as age, sex, family data, and genetic data. A global feature vector formed by concatenating PF and CF-TF may be referred to as a feature vector PF-CF-TF.

In a block 167, controller 50 processes feature vector SCEDM-F(K) or feature vector GF(G) to determine whether CE-ROI 202 comprises a malignancy. In an embodiment, processing the feature vector comprises operating on the feature vector using a classifier such as a support vector machine (SVM) or a neural network (NN) that has been trained on a set of training images CE-ROIs.

Controller 50 may determine a number M, and which of the components of the T components of histogram HTV(T) determined for CE-ROI 202 in block 161 of flow diagram 140, are to be selected for components of texture feature vector TF(M) by processing a plurality of sample CE-ROIs for which it is known whether they are benign or malignant. FIG. 2B shows a flow diagram of a procedure 180 illustrating a procedure by which controller 50 may determine how many, and which components of HTV(T) to select for texture feature vector TF(M), in accordance with an embodiment of the disclosure. Procedure 180 also provides an SVR machine for classifying CE-ROIs responsive to a texture feature vector TF(M) based on the number and components of HTV(T) selected by the procedure for features of TF(M).

Figure 2A:
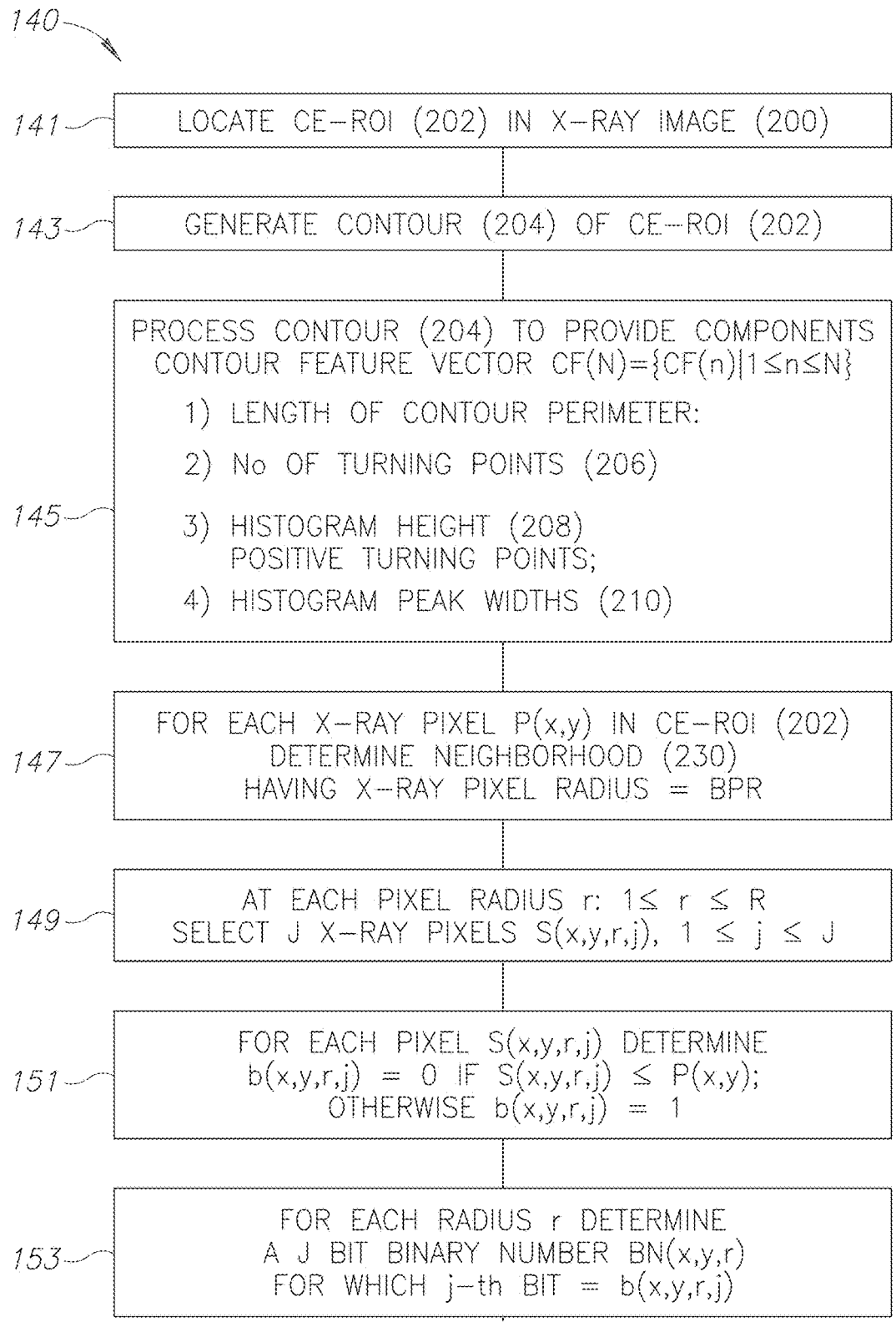
FIG. 2A shows a flow diagram of a procedure by which a XBI processes an SCEDM image of a breast to generate and use a feature vector to determine whether the image indicates presence of malignancy in the breast, in accordance with an embodiment of the disclosure.
Figure 2B:
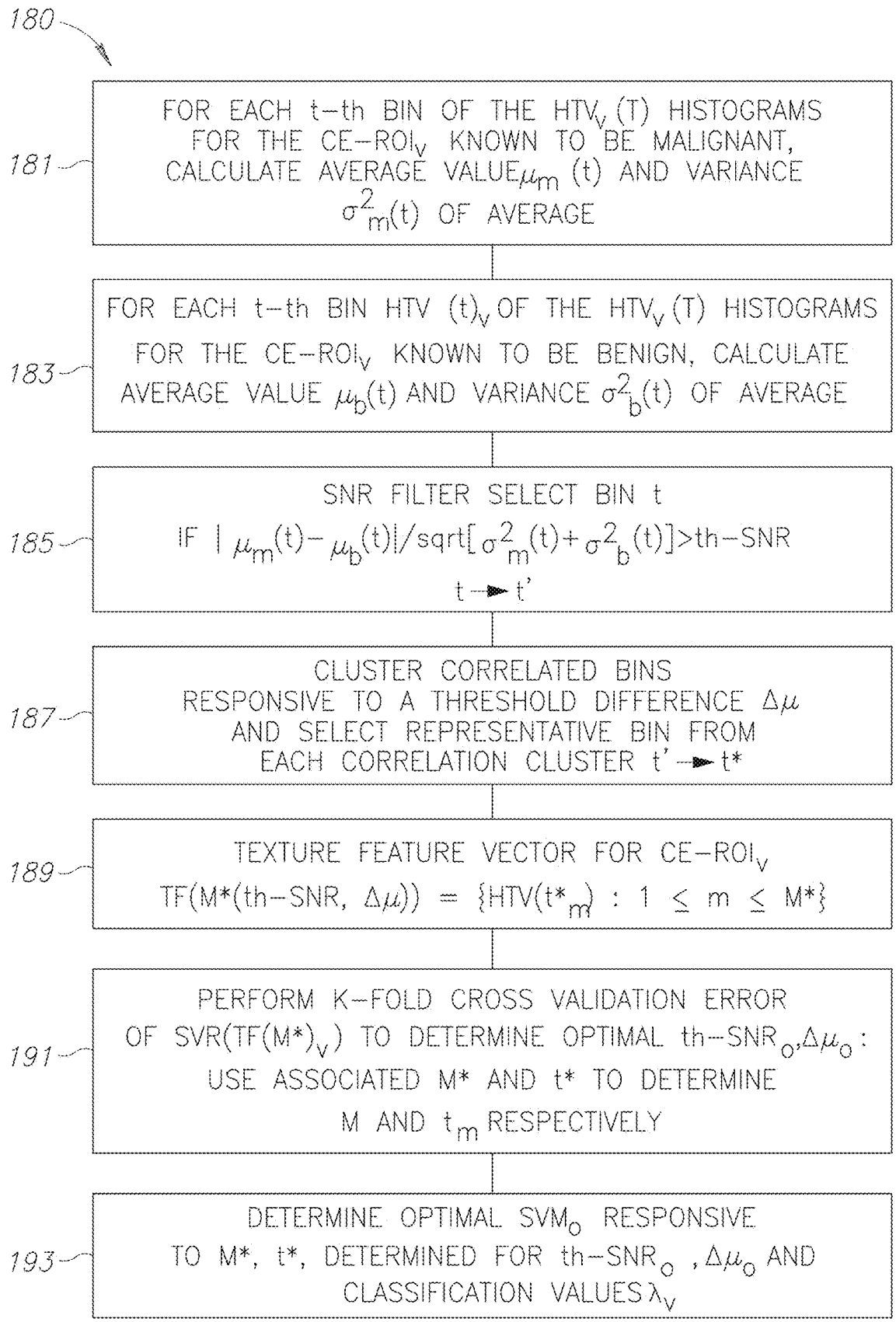
FIG. 2B shows a flow diagram of a procedure by which a XBI may configure a texture feature vector for use with the procedure illustrated in FIG. 2A in diagnosing malignancy, in accordance with an embodiment of the disclosure.

Assume that the sample CE-ROIs are represented by CE-ROI$_v$, 1≤v≤V, and that for each CE-ROI$_v$ controller 50 has acquired a histogram HTV$_v$(T), optionally in accordance with block 159 of procedure 140 shown in FIG. 2A. Assume further that of the V samples CE-ROI$_v$, Vm are known to be malignant and Vb are known to be benign and that V=Vm+Vb.

In a block 181 of flow diagram 180, controller 50 calculates an average value μm(t)=(1/Vm) $\Sigma_1^{Vm}$ HTV$_v$(t) and a variance $\sigma^2_m$(t) of the average, for each t-th bin of the Vm histograms determined for the CE-ROI$_v$ that are known to be malignant. In a block 183 controller 50 calculates an average value μb(t)=(1/Vb) $\Sigma_1^{Vb}$ HTV$_v$(t) and a variance $\sigma_b$(t) of the average, for each t-th bin of the Vb histograms determined for the CE-ROI$_v$ that are known to be benign. In a block 185, the controller may calculate for each t-th bin of the HTV$_v$(T) a signal to noise ratio, "SNR(t)", which may be defined by an expression SNR(t)=|μ$_m$(t)−μ$_b$(t)|/sqrt[$\sigma^2_m$(t)+$\sigma^2_b$(t)], and if SNR(t) is greater than a threshold noise, "th-SNR", the controller selects the t-th bin as a candidate for providing a component of TF(M). Let an SNR selected bin number t be primed and represented by t' to indicate that it was selected. For example if a bin number 783 was selected it is represented by 783'.

Optionally, in a block 187, controller 50 clusters bins having SNR selected bin numbers t' into clusters of correlated bins responsive to a correlation threshold "th-correlation". Bins that are considered to be correlated are clustered in a same i-th correlation cluster. For each i-th correlation cluster a representative bin number t* is selected from the bin numbers t' in the correlation cluster. This correlation process determines, a selection of M* bins having bin numbers t*$_m$, 1≤t*≤M*, selected to provide values HTV$_v$(t*) for texture feature vectors TF(M*)$_v$ for CE-ROI$_v$ respectively. M* is a function of th-SNR and th-correlation, and may be written M*(th-SNR, th-correlation) to indicate the dependence. In a block 191 controller 50 optionally generates a texture feature vector TF(M*(th-SNR, th-correlation)) comprising a set {HTV(t*$_m$): 1≤m≤M*} as components, where t*m represents a particular representative bin number of the M* different representative bin numbers.

In a block 191, controller 50 may perform a K-fold cross validation error evaluation for an SVR model, SVR(TF(M*)$_v$) for the samples CE-ROI$_v$ and their known presence or absence of malignancy using the texture feature vectors TF(M*)$_v$ determined for each of a group of a different pairs of values for th-SNR and th-correlation. A pair of values th-SNR and th-correlation from the group that provides a minimum cross validation error in diagnosing malignancy in the CE-ROI$_v$ may be determined as an optimal pair of values, th-SNR$_o$ and th-correlation$_o$. M* and bin numbers t$_m$* associated with th-SNR$_o$ and th-correlation$_o$ are used as the number M and bin numbers t$_m$ to define texture feature vector in TF(M) in block 161 of flow diagram 140.

In an embodiment, in a block 193, classification values $\lambda_v$ for CE-ROI$_v$, 1≤v≤V respectively generated by the K-fold cross-validation performed for th-SNR$_o$ and th-correlation$_o$, may be used to determine a corresponding optimal SVM$_o$ based on all V members of the plurality of samples CE-ROI$_v$. In an embodiment of the disclosure SVM$_o$ may be used to diagnose a CE-ROI of a breast X-ray image that XBI 20 acquires for a patient to classify and determine if the CE-ROI is malignant.

Figure 5:
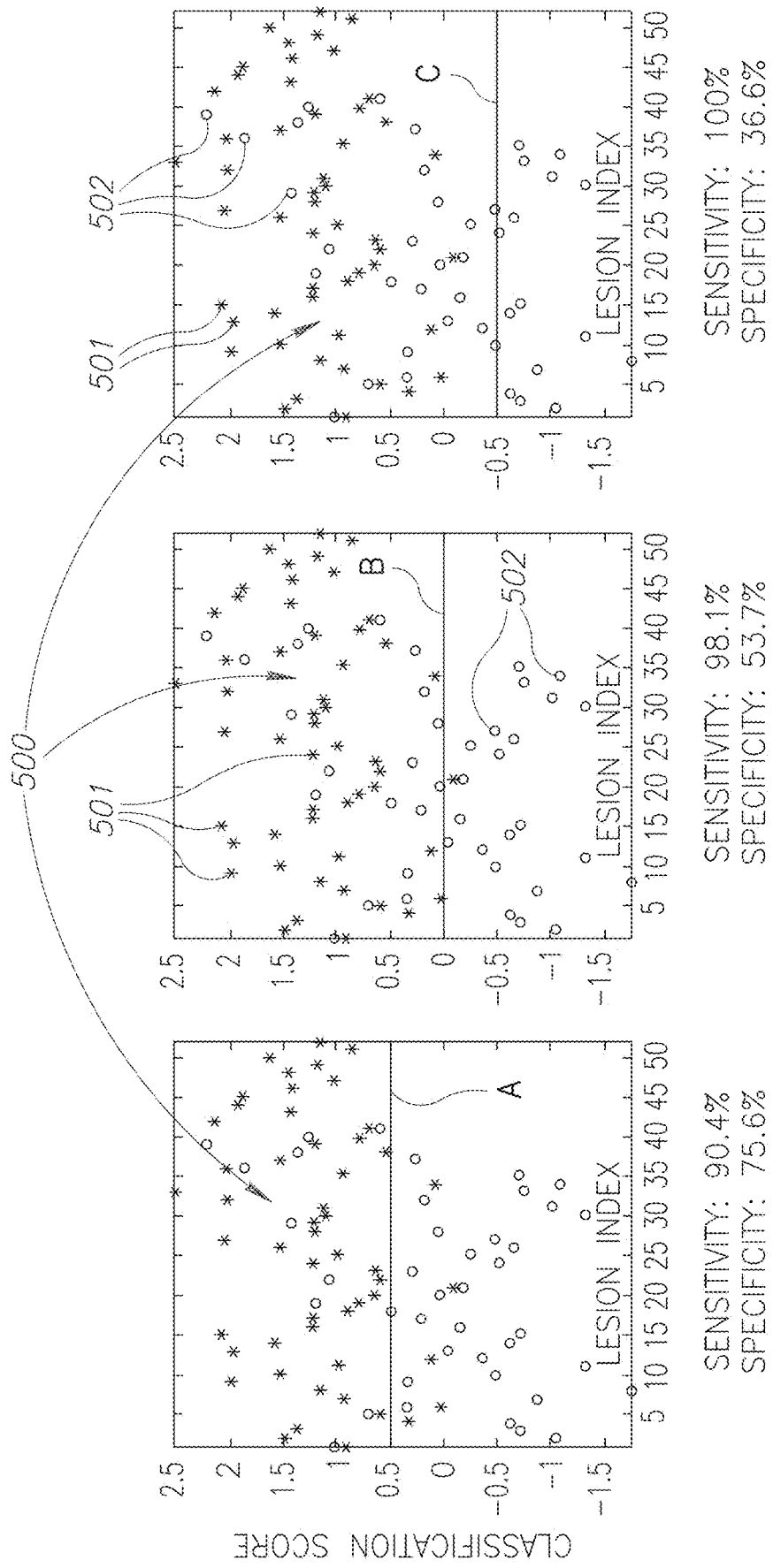
FIG. 5 shows a distribution of classification scores generated responsive to texture feature vector TFs determined for CE-ROIs in SCEDM X-ray images acquired for patients for which biopsies were preformed, and different threshold values for determining whether the scores indicate malignancy, in accordance with an embodiment of the disclosure.

FIGS. 5A-5C show dispersion graphs of results of using a texture feature vector TF(M) and a SVM$_o$ determined in accordance with procedures similar to procedures 140 and 180 shown in the flow diagrams of FIGS. 2A and 2B to classify 93 CE-ROIs segmented by hand from X-ray images acquired for actual patients. The dispersion graphs were generated for texture feature vector, TF(M), parameters: BPR=64 pixels; R=4, PR(1), . . . , PR(4) equal to 15, 30, 45, and 70 pixels, and J=8; M=M*=3 and associated bin numbers t*$_m$=30, 784, and 896 from a histogram HTV(T). Of the 93 CE-ROIs, 41 were known to be images of benign tissue and 52 were known to be images of malignant tissue.

Each of FIGS. 5A-5C shows a same dispersion 500. In the dispersion graphs, CE-ROIs known to be cancerous are represented by asterisks 501. CE-ROIs known to be benign are represented by circles 502. The 52 cancerous CE-ROIs are identified by ID indices 1-52 and the benign CE-ROIs are identified by ID indices 1-41. The abscissas in the dispersion graphs show the ID indices of the CE-ROIs associated with the asterisks and circles. The ordinates of the dispersion graphs show the classification scores determined for the CE-ROIs by the SVM$_o$. Cancerous CE-ROIs have higher classification scores than benign CE-ROIs. Dispersion graphs 5A-5C have classification decision lines A-C respectively that may be used to make a decision as to whether a given classification score is to be considered to indicate that an entry in the dispersion graphs is cancerous or not. Classification scores above a given partition line A, B, or C may be considered to indicate that tissue in a CE-ROI represented by an entry in the graph, that is an asterisk or a circle, is malignant, while classification scores below the partition line may be considered to indicate that tissue in the CE-ROI is benign. Classification lines A, B, and C are located at classification scores 0.5, 0, and −0.5.

Graph 5C shows that if the decision line, decision line C in the graph, is set so low as to provide 100% sensitivity, that is, to correctly classify all cancerous CE-ROIs as cancerous, XBI 20 will exhibit specificity of 36.6% and correctly identify 36.6% of the non-cancerous CE-ROIs as benign. Graph 5C indicates that XBI 20 operating in accordance with an embodiment of the disclosure to implement procedures similar to that illustrated by flow diagram 140 and 180, may be configured to provide 100% detection of cancerous lesions and potentially reduce unwanted biopsies by about 36%. Graph 5B, with decision line B at 0, XBI 20 configured in accordance with an embodiment of the disclosure to provide 98% sensitivity will provide specificity of about 53% and potentially reduce unwanted biopsies by about half. Graph 5A indicates that XBI 20 configured in accordance with an embodiment of the disclosure to reduce unwanted biopsies by about 75% will still correctly detect about 90% of cancerous lesions.

Whereas the above description references specific examples of features that may be used to provide components of a feature vector used to classify and distinguish malignant from benign lesions based on contrast enhanced images of the lesions, practice of an embodiment of the disclosure is not limited to the referenced features. By way of example, a feature or any combination of more than one feature listed and defined by the Breast Imaging Reporting and Data System (BIRADS) Lexicon Classification System established by the American College of Radiology may be used to provide a component of a feature vector for classifying a lesion in accordance with an embodiment of the disclosure. The BI-RADS classification system classifies lesions as mass like, three-dimensional space occupying lesion, or a non-mass like lesion and for each type of lesion a characteristic of the lesion that may be used to provide a determination as to whether the lesion should be classified as malignant or benign. Among the characteristics of a mass like lesion listed and defined in the BIRADS lexicon are by way of example, characteristics of the lesion's shape—whether it is round, oval or irregular, and characteristics of its margin—whether the margin appears smooth, irregular or spicualted. Among characteristics of a non-mass-lesion listed and defined in the BIRAD lexicon are by way of example, characteristics of its distribution—whether it is characterized by a focal area, whether is linear, ductal, segmental or diffuse. Furthermore, whereas a classifier may provide classification scores such as those shown in FIGS. 5A-5C to determine whether a CE-ROI comprises a cancer, in an embodiment, the classifier may operate on a feature vector to provide BIRADS scores for use in determining whether a breast lesion is cancerous or not.

In an embodiment, a feature of a feature vector may be a time dependent feature. For example, as described with reference to FIGS. 1A-1B, XBI 20 may be operated to acquire a plurality of SCEDM images. The images, by way of example, low and high energy MLO X-ray images and low and high energy CC X-ray images may be acquired at different times. During time lapses between acquisitions of the images concentration of a contrast agent introduced into a patient's body may change as a result of a rate at which the contrast agent is taken up or washed out by breast tissue that is being imaged. A rate of increase or decrease of the contrast agent in the imaged tissue may be estimated from a change in contrast of the imaged tissue exhibited in the images and used to provide a component of a feature vector for discriminating malignant from benign tissue in accordance with an embodiment.

For example, a time lapse between acquiring CC and MLO X-ray images of a breast tissue lesion may be as long as 1-2 minutes. If concentration of a contrast agent in the lesion is substantially maximum during acquisition of the CC X-ray images, the concentration may be substantially reduced by wash out at a time at which the MLO X-ray images are acquired. A difference in contrast between the CC and MLO X-ray images, and the time lapse between acquisition of the images may be used to provide an estimate of a rate at which blood flow washes out the contrast agent from the lesion and thereby a characteristic of magnitude of blood flow in and through the lesion. The rate of washout may be advantageous as a component of a feature vector in accordance with an embodiment for distinguishing whether the lesion is malignant or benign.

The above description indicates, by way of example, that identification of a feature of an SCEDM image of a breast tissue lesion for generating or using as a component of a feature vector may be determined manually. In an embodiment a convolutional neural network (CNN) may be used to automatically identify and determine which features of an SCEDM image of a breast tissue lesion are advantageous for providing a component of a feature vector for classifying lesions as malignant or benign. Upon identifying and determining which features of an SCEDM image are advantageous for use as a component of the feature vector, the CNN may provide the feature to a classifier that processes the feature vector to determine malignancy or benignity. Optionally the CNN operates as the classifier, and processes the feature vector to determine malignancy or benignity. The CNN may undergo training to learn directly from input images to identify and determine which features of an SCEDM to provide to a classifier for classifying lesions as malignant or benign.

By way of example, a CNN may be used to determine a magnitude of a washout rate for a CE-ROI by processing SCEDM images comprising the CE-ROI acquired at different times after the CNN was trained on images of malignant breast tissue that exhibit a known rate of washout of a contrast agent. Images used to train the CNN may be SCEDM images of tissue for which information with respect to washout is known from MRI images of the tissue.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the disclosure in the present application are provided by way of example and are not intended to limit the scope of the disclosure. The described embodiments comprise different features, not all of which are required in all embodiments of the disclosure. Some embodiments utilize only some of the features or possible combinations of the features. Variations of embodiments of the disclosure that are described, and embodiments of the disclosure comprising different combinations of features noted in the described embodiments, will occur to persons of the art. The scope of the disclosure is limited only by the claims.

The invention claimed is:

1. Apparatus for diagnosing breast cancer, the apparatus comprising:
a controller having a set of instructions executable to:
acquire a contrast enhanced region of interest (CE-ROI) in an X-ray image of a patient's breast, the X-ray image comprising X-ray pixels that indicate intensity of X-rays that passed through the breast to generate the image;
determine a texture neighborhood for each of a plurality of X-ray pixels in the CE-ROI, the texture neighborhood for a given X-ray pixel of the plurality of X-ray pixels extending to a bounding pixel radius of BPR pixels from the given pixel;
process indications of intensity provided by a plurality of X-ray pixels that are located within the texture neighborhood using a convolutional neural network (CNN) to determine features of the X-ray image for use as components of a texture feature vector (TF) for the texture neighborhood;
generate a texture feature vector comprising the determined features as components; and
use a classifier to classify the texture feature vector TF to determine whether the CE-ROI is malignant.

2. The apparatus according to claim 1 wherein the instructions comprise instructions executable to: select a plurality of R different pixel radii PR(r), $1 \leq r \leq R$, in the texture neighborhood, for which $PR(r) < PR(r+1)$ and $PR(R)=BPR$;
for each radius PR(r) select a number J(r) of X-ray pixels for processing;
determine values for a number of M representative bins of a texture vector histogram HTV(T) having a bin length in number of bins T equal to a sum over r from 1 to R of $2^{\hat{}}(r)$, and values HTV(t) $1 \leq t \leq T$ that are a function of texture vectors TV determined for the texture neighborhoods of a plurality of pixels in the CE-ROI; and
use the values determined for the M representative bins to generate the texture feature vector (TF).

3. The apparatus according to claim 1 wherein the instructions comprise instructions executable to process the X-ray image to locate the CE-ROI.

4. The apparatus according to claim 3 wherein the instructions comprise instructions executable to process the X-ray image to determine a contour for the CE-ROI.

5. The apparatus according to claim 4 wherein the instructions comprise instructions executable to determine a contour feature vector CF based on the determined contour and concatenate the texture feature vector TF and the contour feature vector CF to provide a feature vector CF-TF.

6. The apparatus according to claim 5 wherein the instructions comprise instructions executable to use the feature vector CF-TF to determine whether the CE-ROI is malignant.

7. Apparatus for diagnosing breast cancer, the apparatus comprising:
a controller having a set of instructions executable to:
acquire a contrast enhanced X-ray image of a patient's breast at a plurality of different times, the X-ray image at each time comprising X-ray pixels that indicate intensity of X-rays that passed through the breast to generate the image;
acquire a contrast enhanced image of a region of interest (CE-ROI) in each X-ray image;
for each image of the CE-ROI determine a texture neighborhood for each of a plurality of X-ray pixels in the CE-ROI, the texture neighborhood for a given X-ray pixel of the plurality of X-ray pixels extending to a bounding pixel radius of BPR pixels from the given pixel;
to process the images of the CE-ROI to determine a time dependent feature of the CE-ROI and use the time dependent feature as a feature of a texture feature vector (TF) for the CE-ROI; and
use a classifier to classify the TF to determine whether the CE-ROI is malignant.

8. The apparatus according to claim 7 wherein the time dependent feature is a rate of increase of a contrast agent taken up by tissue imaged in the CE-ROI.

9. The apparatus according to claim 7 wherein the time dependent feature is a rate of decrease of a contrast agent washed out from tissue imaged in the CE-ROI.

10. Apparatus for diagnosing breast cancer, the apparatus comprising:
a controller having a set of instructions executable to:
acquire a contrast enhanced region of interest (CE-ROI) in an X-ray image of a patient's breast, the X-ray image comprising X-ray pixels that indicate intensity of X-rays that passed through the breast to generate the image;
determine a texture neighborhood for each of a plurality of X-ray pixels in the CE-ROI, the texture neighborhood for a given X-ray pixel of the plurality of X-ray pixels extending to a bounding pixel radius of BPR pixels from the given pixel;
generate a texture feature vector (TF) having components based on the indications of intensity provided by a plurality of X-ray pixels in the CE-ROI that are located within the texture neighborhood; receive a profile feature vector (PF) of the patient, concatenate the PF with the TF to provide a feature vector PF-TF and use a classifier to classify the PF-TF to determine whether the CE-ROI is malignant.

11. The apparatus according to claim 1 wherein the wherein the classifier generates a Breast Imaging Reporting and Data System (BIRADS) Lexicon Classification System code for the CE-ROI to provide an indication as to whether the CE-ROI comprises a malignancy.

12. The apparatus according to claim 1 wherein the wherein the classifier comprises a support vector machine and/or a neural network.

13. The apparatus according to claim 1 wherein the X-ray image is a spectral contrast enhanced digital mammography (SCEDM) image.

* * * * *